United States Patent
Iannotti

(10) Patent No.: US 9,512,445 B2
(45) Date of Patent: Dec. 6, 2016

(54) HUMERAL JOINT REPLACEMENT COMPONENT

(75) Inventor: Joseph P. Iannotti, Strongsville, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 1503 days.

(21) Appl. No.: 12/780,051

(22) Filed: May 14, 2010

(65) Prior Publication Data

US 2011/0054624 A1 Mar. 3, 2011

Related U.S. Application Data

(60) Provisional application No. 61/238,429, filed on Aug. 31, 2009.

(51) Int. Cl.
*A61F 2/40* (2006.01)
*C12N 15/86* (2006.01)

(52) U.S. Cl.
CPC ..... *C12N 15/86* (2013.01); *C12N 2770/24243* (2013.01)

(58) Field of Classification Search
CPC .............. A61F 2/40; A61F 2002/30538; A61F 2002/4018–2002/4025; A61F 2002/4029–2002/4055
USPC ...................... 623/19.11–19.14, 22.21–22.23, 22.11, 623/22.15, 22.17–22.19
See application file for complete search history.

(56) References Cited

U.S. PATENT DOCUMENTS

| 4,261,062 | A |   | 4/1981  | Amstutz |                |
|-----------|---|---|---------|---------|----------------|
| 5,370,703 | A | * | 12/1994 | Willert et al. | 623/22.22 |
| 6,187,050 | B1| * | 2/2001  | Khalili et al. | 623/22.22 |
| 6,197,063 | B1|   | 3/2001  | Dews    |                |
| 6,537,321 | B1| * | 3/2003  | Horber  | 623/22.22      |
| 6,610,095 | B1|   | 8/2003  | Pope    |                |
| 6,699,289 | B2|   | 3/2004  | Iannotti|                |
| 6,736,851 | B2|   | 5/2004  | Maroney |                |
| 6,875,234 | B2|   | 4/2005  | Lipman  |                |
| 6,942,699 | B2| * | 9/2005  | Stone et al. | 623/19.14 |
| 7,338,498 | B2|   | 3/2008  | Long    |                |
| 7,431,736 | B2|   | 10/2008 | Maroney |                |
| 7,510,558 | B2|   | 3/2009  | Tallarida |              |
| 7,527,631 | B2|   | 5/2009  | Maroney |                |

(Continued)

FOREIGN PATENT DOCUMENTS

| EP | 1996123 A2 | 12/2008 |
|----|-----------|---------|
| EP | 1996124 A2 | 12/2008 |

(Continued)

OTHER PUBLICATIONS

ISR International Search Report for PCT/US2010/046920, mailed May 30, 2011.

(Continued)

*Primary Examiner* — Christopher D Prone
(74) *Attorney, Agent, or Firm* — Tarolli, Sundheim, Covell & Tummino LLP

(57) ABSTRACT

A humeral prosthetic head has a non-spherical articulation surface coupled with an intermediate component connecting the head and the humerus, the intermediate component connected to the epiphysis, metaphysis, or diaphysis, or to one or more additional components connected to the humerus. The intermediate portion provides for axial and angular offset of the head with respect to a connection to the humerus, using a curvilinear tapered engagement.

9 Claims, 13 Drawing Sheets

(56) References Cited

U.S. PATENT DOCUMENTS

| | | |
|---|---|---|
| 7,604,665 B2 | 10/2009 | Iannotti |
| 2003/0125809 A1 | 7/2003 | Iannotti |
| 2003/0191537 A1 | 10/2003 | Wasielewski |
| 2004/0015170 A1 | 1/2004 | Tallarida |
| 2004/0193168 A1 | 9/2004 | Long |
| 2004/0193175 A1 | 9/2004 | Maroney |
| 2004/0193275 A1 | 9/2004 | Long |
| 2004/0193276 A1 | 9/2004 | Maroney |
| 2004/0193278 A1 | 9/2004 | Maroney |
| 2004/0210317 A1 | 10/2004 | Maroney |
| 2005/0143829 A1 | 6/2005 | Ondria |
| 2005/0197708 A1 | 9/2005 | Stone |
| 2006/0074430 A1 | 4/2006 | Deffenbaugh |
| 2006/0149390 A1 | 7/2006 | Long |
| 2006/0241775 A1 | 10/2006 | Buss |
| 2007/0162141 A1 | 7/2007 | Dews |
| 2007/0179608 A1 | 8/2007 | Ek |
| 2007/0225818 A1 | 9/2007 | Reubelt |
| 2008/0065226 A1 | 3/2008 | Long |
| 2008/0140209 A1 | 6/2008 | Iannotti |
| 2008/0140211 A1 | 6/2008 | Doubler |
| 2008/0172125 A1 | 7/2008 | Ek |
| 2008/0195220 A1 | 8/2008 | Pope |
| 2008/0269906 A1 | 10/2008 | Iannotti |
| 2009/0187193 A1 | 7/2009 | Maroney |
| 2009/0254188 A1 | 10/2009 | Maroney |
| 2010/0016975 A1 | 1/2010 | Iannotti |

FOREIGN PATENT DOCUMENTS

| | | |
|---|---|---|
| EP | 1996125 A2 | 12/2008 |
| WO | WO2007109319 B1 | 6/2007 |
| WO | WO2007109291 A2 | 9/2007 |
| WO | WO2007109291 A3 | 9/2007 |
| WO | WO2007109291 B1 | 9/2007 |
| WO | WO2007109319 A2 | 9/2007 |
| WO | WO2007109319 A3 | 9/2007 |
| WO | WO2007109340 A2 | 9/2007 |
| WO | WO2007109340 A3 | 9/2007 |

OTHER PUBLICATIONS

Written Opinion of the International Search for PCT/US2010/046920, mailed May 30, 2011.

U.S. Appl. No. 61/238,429, filed Aug. 31, 2009, Iannotti.

J. Iannotti, et al., The Normal Glenohumeral Relationships, The Journal of Bone and Joint Surgery, 11 Pages, vol. 74-A, No. 4 (Apr. 1992).

www.zimmer.com.au—Flatow Shoulder Replacement, Retrieved May 19, 2010.

* cited by examiner

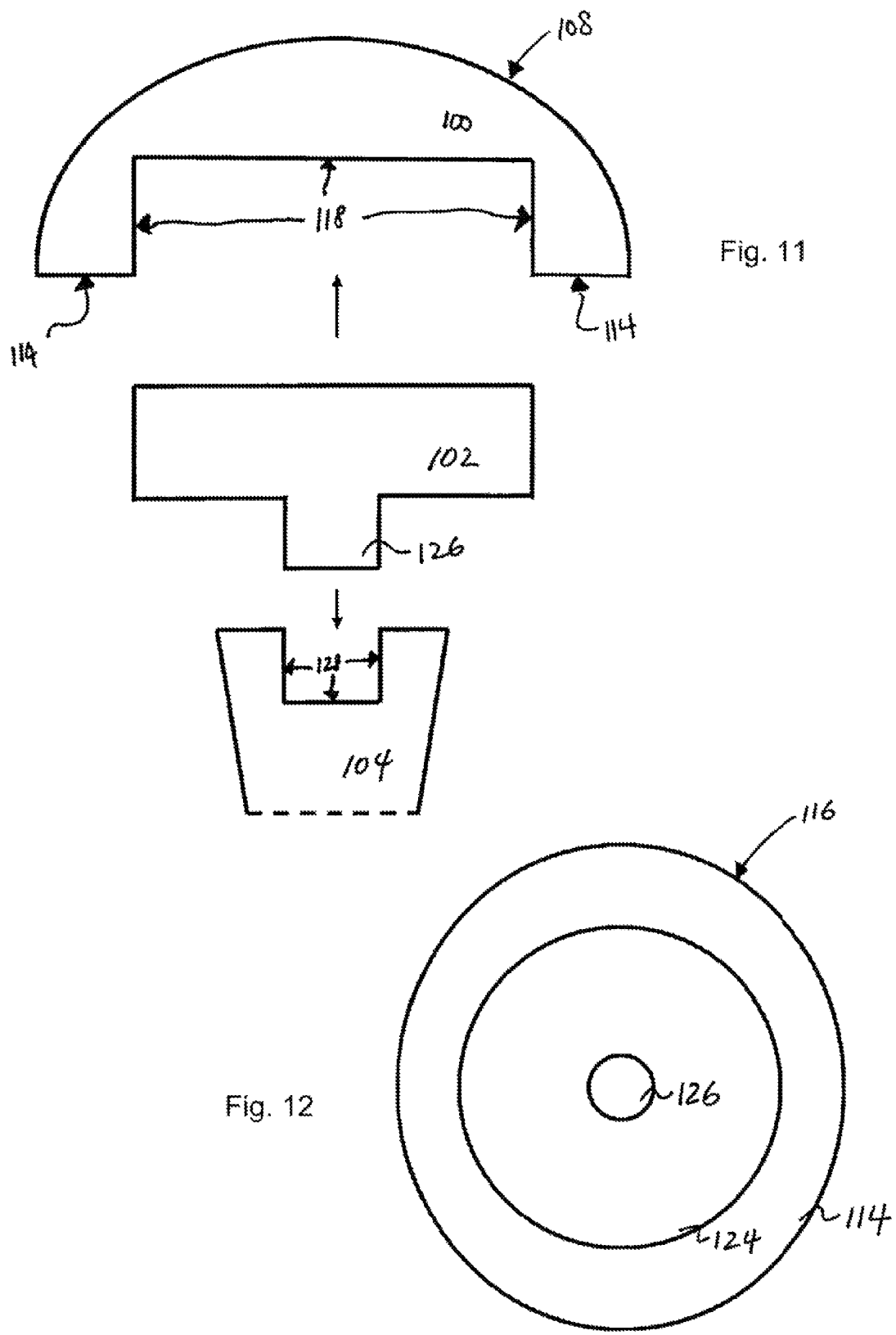

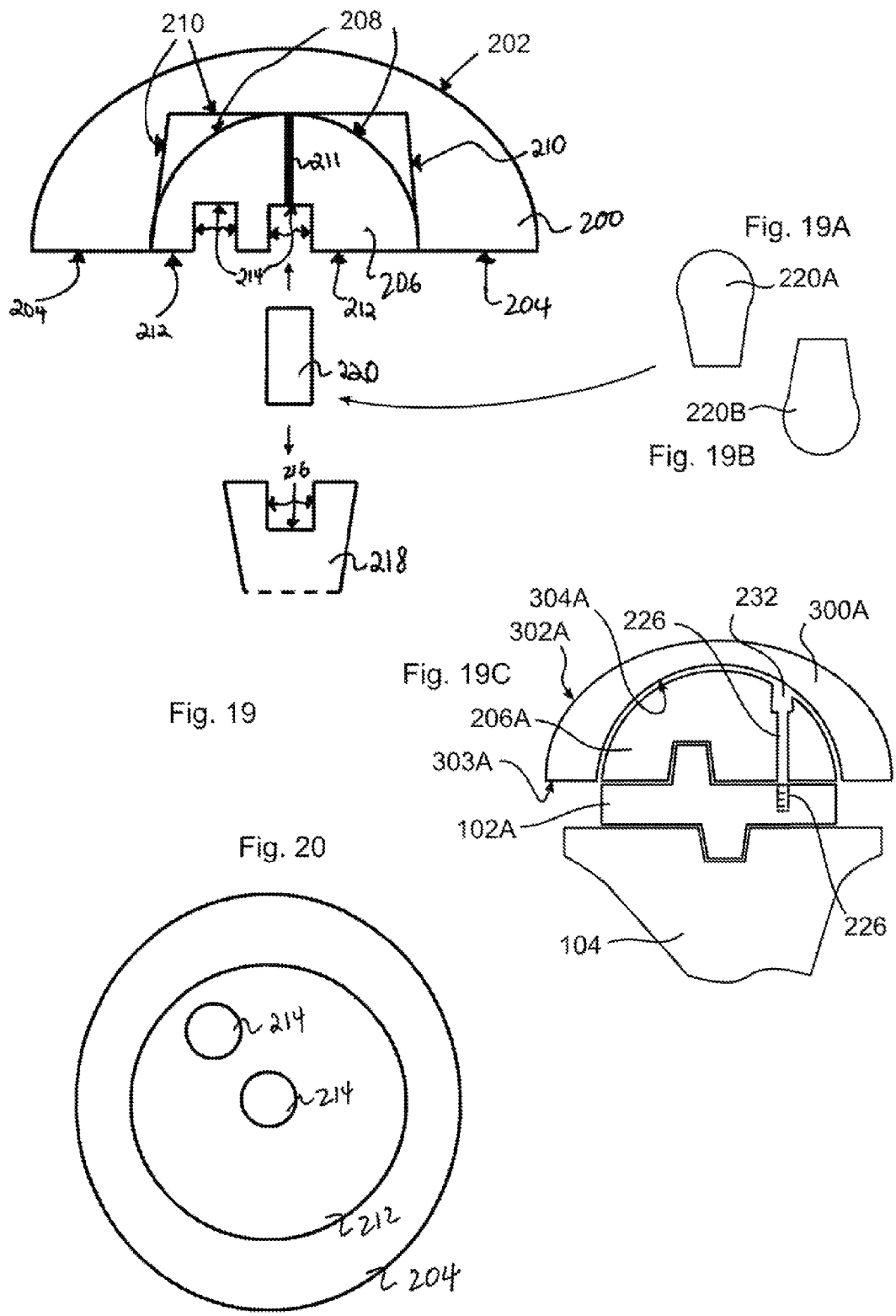

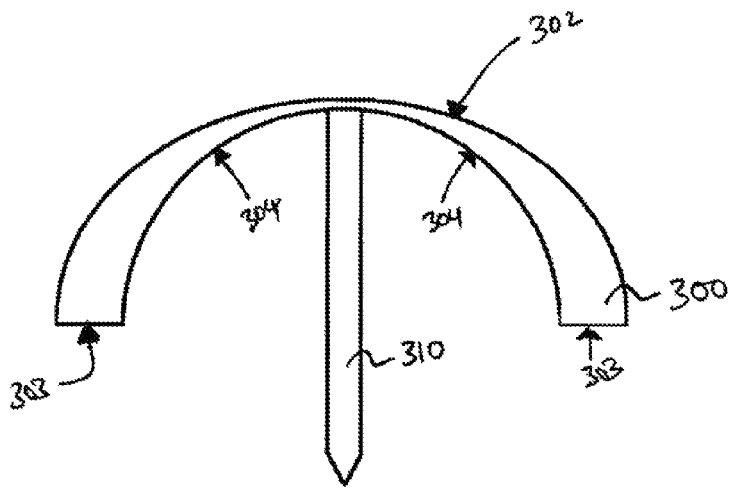
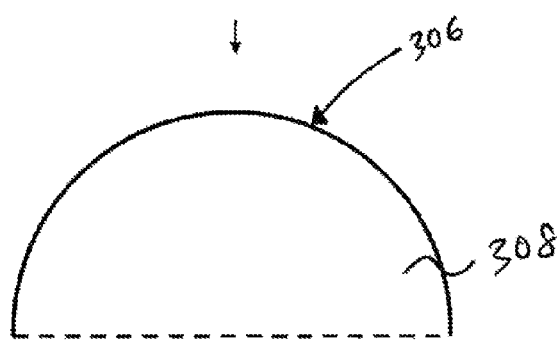
Fig. 21
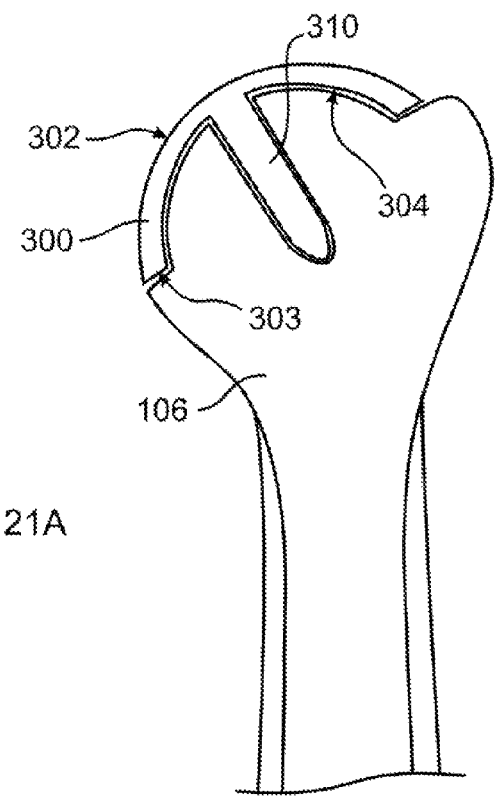
Fig. 21A

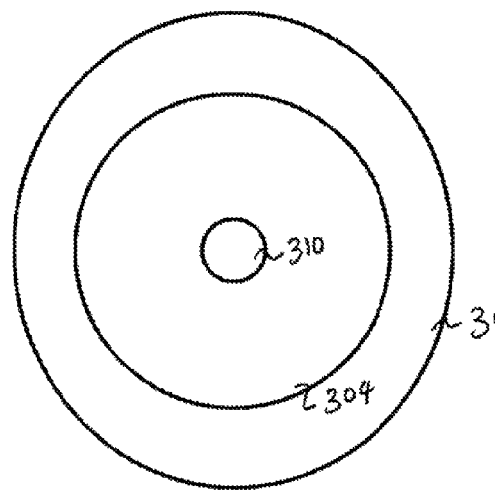
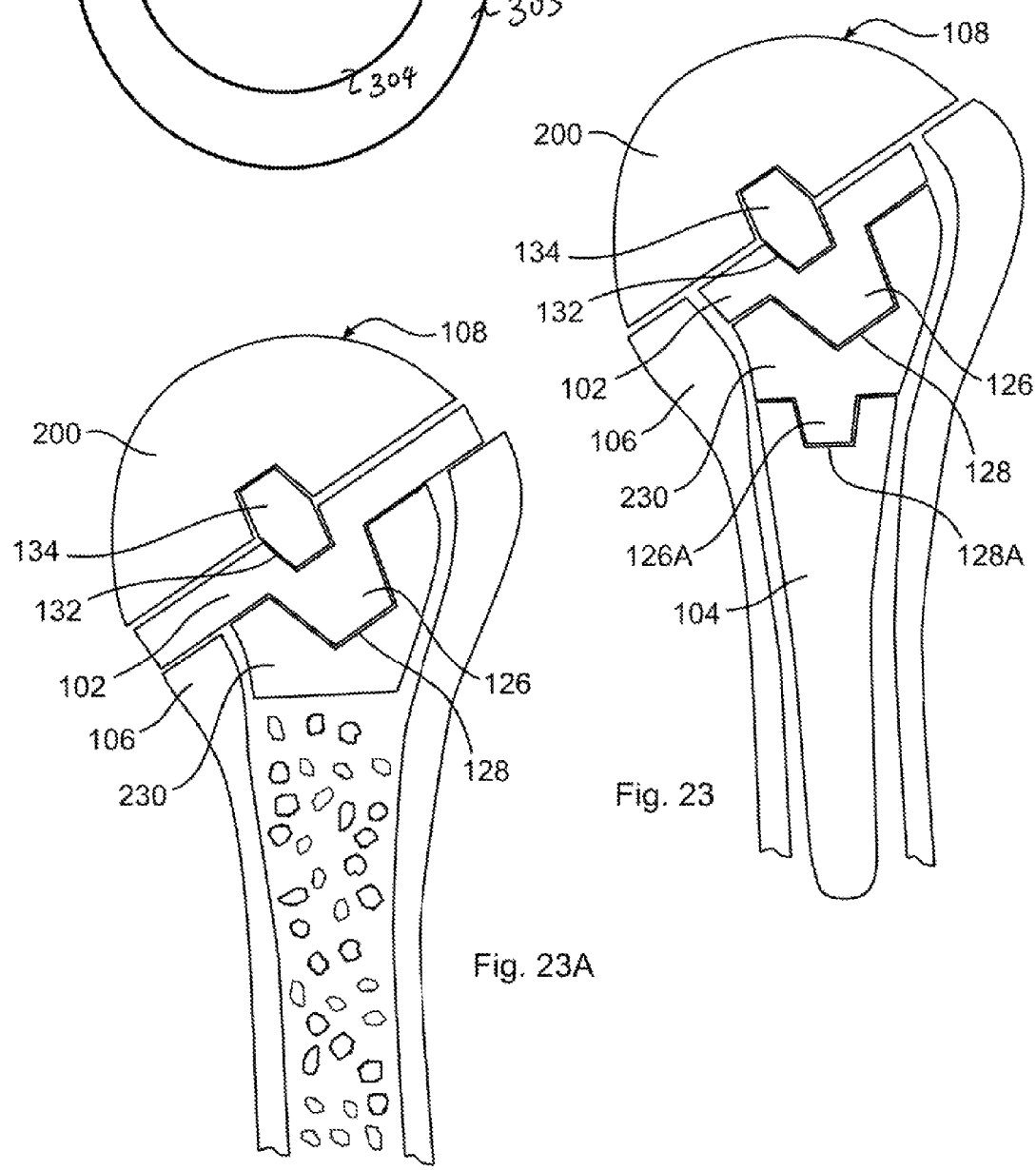
Fig. 22
Fig. 23
Fig. 23A

HUMERAL JOINT REPLACEMENT COMPONENT

CROSS REFERENCE TO RELATED APPLICATIONS

This application claims the benefit of U.S. Provisional Application 61/238,429, filed Aug. 31, 2009.

FIELD OF INVENTION

The present invention relates to the field of joint replacement and/or resurfacing, and more particularly total shoulder arthroplasty or hemiarthroplasty using a stemmed or humeral resurfacing prosthetic.

BACKGROUND OF THE INVENTION

Normal shoulder kinematics allows for translational motion of the humeral head within the glenoid particularly at the end ranges of passive motion. These translations can be several millimeters and are thought to be due to capsular tightening on the opposite side of the direction of humeral head translation. Small amounts of translational motion also occur with active range of motion and are correlated with the degree of mismatch in the radii of curvature between the humeral head and glenoid. The native articular surface of the humeral head is not spherical in shape. Nevertheless, it is believed the central portion of the native humeral head is spherical and its curvature then decreases out toward the periphery. In fact, one study shows that the native humeral head of adults has a shape of a semi-ellipsoid with its anterior to posterior radius of curvature being approximately 2-3 mm less than its superior to inferior radius of curvature. See J. Iannotti, J. Gabriel, S. Schneck, B. Evans, and S. Misra, The Normal Glenohumeral Relationships, The Journal of Bone and Joint Surgery, Vol. 74-A, No. 4 (April 1992). The effect of a semi-ellipsoid native humeral head shape on the kinematics of the shoulder joint has not been well defined. Based upon the kinematics of the knee and femoral condyle anatomy, it would be suspected that asymmetric radii of curvature would allow for roll or translational motion of one surface on the other. It has been my long standing hypothesis that a semi-ellipsoid humeral prosthetic head design may allow for humeral head translation on the glenoid. This concept becomes important in prosthetic arthroplasty because translational motion of the humeral head and mismatch of the radii of curvature play an important role in wear and loosening of the glenoid component as well as the materials that can be used for a load bearing surface.

In conventional shoulder prosthetic designs, the humeral prosthetic head is spherical in shape and normal translational motion is allowed by a larger radius of curvature of the glenoid component. Although this will allow for translation before rim loading thereby decreasing the risk of loosening, it also increases the stress per unit area increasing the wear potential. In addition mismatched radii of curvature prevent the use of metal on metal or ceramic bearing surfaces and limits the materials to metal on plastic. One concept to manage or address the issue for allowing for humeral head translation versus decreased surface contact area is the biconcave glenoid design with a spherical head in the Bigliani Flatow shoulder. This design proposed to improve wear characteristics when there is perfect conformity with the arm through a mid range of motion, when the radius of curvature of the center of the glenoid was equal to that of the spherical humeral head, yet allowing for translation at the end ranges of motion when the radius of curvature of the glenoid increased. With use of the shoulder it has been suspected that the subtle differences in the radii of curvature of the poly glenoid would be lost due to plastic deformation of the part resulting in a uniform radius.

A requirement of humeral prosthetic surgery and design is the need to precisely place the prosthetic within the area defined by the humeral osteotomy and to reproduce the center of rotation of the normal native humeral head of a patient. When using a resurfacing component proper placement can be achieved by the surgical technique when choosing the site for preparing the humeral head. For a stemmed arthroplasty, this is achieved by surgical technique as well as prosthetic design which may require an eccentric taper. An eccentric taper on a spherical head can be effective in placement of the humeral prosthetic head in the optimal position within the plane of the humeral osteotomy by rotation of the humeral prosthetic head.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

SUMMARY OF THE INVENTION

In accordance with one embodiment of the invention, a humeral prosthetic provides a non-spherical humeral head, having the shape of an ellipsoid, defined as a superior to inferior (SI) radius of curvature being greater than an anterior to posterior (AP) radius of curvature. The elliptical head of the invention may replace the entire or a portion of the native humeral head. The articulating surface can be affixed to the humerus by used of a stemmed component which in turn is fixed to the metaphyseal and/or diaphyseal part of the humeral shaft. The invention provides either a humeral hemiarthroplasty (articulation with the native glenoid) or with articulation with a prosthetic glenoid component. The ratio of major and minor curvature of the articulating surface is varied to supply a spectrum of anatomic shapes and sizes of humeral head components, for example in the form of a kit, which may be conveniently available in an operating theatre.

A variety of related devices and methods have been disclosed by the inventor, for example as may be found in U.S. Patent Publications 2010/0016975, 2009/0254188, 2009/0187193, 2008/0269906, 2008/0140209, 2008/0065226, 2006/0149390, 2006/0074430, 2005/0143829, 2004/0193278, 2004/0193276, 2004/0193275, 2004/0193175, 2004/0193168, 2003/0125809, 2004/0210317, and U.S. Pat. Nos. 7,604,665; 7,527,631; 7,338,498; 6,699,289; 7,431,736, the contents of each of which are incorporated by reference herein.

Positioning of the humeral head component onto the stem is advantageously accomplished using an intermediate component that may be provided in a a variety of embodiments, described further herein. The intermediate piece is advantageously, but not necessarily, centered within the elliptical humeral head. The intermediate piece allows for rotation within the elliptical head and allows the head component to be positioned onto the humeral surface without changing the orientation of the SI and AP dimension of the head, with respect to the SI and AP dimensions of the humeral osteotomy surface. The intermediate piece advantageously includes a locking mechanism, for example a standard or Morse taper.

The stem surface of the intermediate piece has a centered or eccentric male or female Morse taper connection so that rotation of the intermediate piece between the head or between the stem will allow for translation of the humeral head segment within the plane of the intermediate piece, while maintaining the anatomic orientation of the major and minor axis of curvature of the articular surface of the elliptical head.

The device advantageously contains a non spherical modular humeral head articulation having the shape of an ellipsoid such that the superior to inferior radius of curvature is greater than the anterior to posterior radius of curvature. Its central portion, typically two thirds in humans, may be spherical or may have also have an elliptical shape.

The articulating component contacts the native glenoid, in a hemiarthroplasty, or with a glenoid component, in a total shoulder arthroplasty (TSA). With respect to a TSA, the glenoid component may contain a radius of curvature that is equal to the radius of curvature of the central portion of the humeral head or have an intentionally larger radius of curvature of the humeral head.

After the native humeral head, or a portion thereof, is removed, the elliptical prosthetic humeral head can be placed onto a stem component that obtains its fixation within the metaphysis and/or diaphysis of the humeral canal/shaft. The stem component can achieve fixation by press fit, porous coated biologic fixation, cement fixation, or any other suitable means. The stem component can be contained within the metaphysis only or within the metaphysis and diaphysis of the humerus.

As noted above, positioning of the elliptical prosthetic humeral head to the stem is advantageously accomplished using an intermediate piece having several alternative embodiments, described herein.

In one embodiment, a spherical disc is centered within the elliptical head and can rotate within the outer elliptical shell. An outer dimension of the intermediate piece is a Morse taper that can be locked within the outer articulating piece through impaction of the Morse taper. The intermediate piece connects with the stem using a male or female, centered or eccentric, Morse taper on its stem side that connects to a corresponding female or male Morse taper on the proximal end of the stem. Eccentric tapers can be located in any of a variety of locations that are offset from a central axis, and alternative pieces may be made available at the time of surgery, to increase options for the practitioner.

Rotation of the intermediate piece about the eccentric taper connecting the intermediate piece with the stem will result in translation of the elliptical head within the plane of the intermediate piece, for example the humeral osteotomy surface, while allowing for the major and minor axes (curvatures) of the elliptical head to remain positioned in the desired anatomic orientation prescribed by the patients anatomy.

In another alternative, an intermediate piece design includes a connection of the intermediate piece with a fourth element. The intermediate piece has a female Morse taper (centered or eccentric) and the proximal end of the stem also has a female Morse taper. The intermediate piece and stem are connected by a fourth component having a fixed angle (e.g. double male Morse taper) or a variable angle (e.g. ball taper male taper having its ball taper on either the stem or intermediate piece female taper).

In yet another embodiment of the invention, the intermediate piece is positioned within the humeral metaphysis, below the surface of the osteotomy, and below the stem side of the elliptical humeral articulating component. In this embodiment, the humeral stem is inserted sufficiently below the humeral osteotomy surface to allow for placement of the intermediate piece. The intermediate piece has a male Morse taper on the stem side and a male or female (centered or eccentric) Morse taper on the humeral head side. The intermediate piece can rotate about the stem before being locked in place. With an eccentric Morse taper on its humeral head side the articulating component can be translated within the plane of the intermediate piece, that is, a plane corresponding to the osteotomy surface.

In a further embodiment, an intermediate piece connects to a stem as described elsewhere, however the humeral head side of the intermediate piece, and the elliptical humeral head component, has a female centered or eccentric Morse taper. The intermediate and humeral articulating components are connected with a double male (fixed angle) or variable angle (ball) taper. The ball taper can be placed within the intermediate or the humeral head piece and provides variable angulation between the intermediate piece and the humeral head component.

An alternative embodiment provides an intermediate piece having a convex spherical shape that is placed within a large female Morse taper in the outer shell of the articular component. In this design the articular component can be elliptical or spherical in shape. After angular positioning of the articulating component, using the infinite variation permitted within the range, within the intermediate piece, the components are impacted thereby locking then in place. The intermediate piece becomes contained within the central portion of the elliptical humeral head. The stem surface of the intermediate piece has female or male centered or eccentric, Morse taper, and is connected to the proximal stem via corresponding male or female tapers, respectively. Both the stem and the stem side of the intermediate piece advantageously, for example, have a female Morse taper connecting each member with a double male Morse taper.

In a further embodiment, the intermediate piece is a dome shaped convex spherical design that is contained within a mated concave spherical surface within the humeral head, which has an elliptical articulating surface. The intermediate piece is rotatable around the spherical surface, yielding infinite variability within a range of angulations of the outer elliptical, or outer articulating, surface segment. The intermediate convex surface is locked into a concave articulation with a screw or other locking mechanism, as would be understood by one skilled in the art. The stem side of the intermediate piece advantageously has a centered or eccentric male or female Morse taper, that connects to a corresponding female or male Morse taper, on the proximal end of the stem. An alternative is a female Morse taper on both the stem side of the intermediate piece and the proximal end of the stem. A double Morse taper connects to the intermediate part, and thus connects the attached elliptical or spherical head onto the stem.

The articulations materials may be metallic, polymeric, ceramic, composite, or a combination of materials, as would be understood by one skilled in the art, or may be constructed using materials that are not yet known.

In another embodiment of the invention, the elliptical humeral head shape is advantageously applied in a surface replacement procedure to replace the humeral surface. The embodiment contemplates the use of a non-spherical humeral head articulation having the shape of an ellipsoid, such that the superior to inferior radius of curvature is greater than the anterior to posterior radius of curvature. The implant obtains its fixation from an interference fit of a back side of a porous coated prosthetic, and a machined (reamed) convex surface of a remaining humeral head. A small stem contained within the epiphyseal portion of the humeral head is an optional means of fixation. The stemmed portion of the articular shell can be modular, or may be fixed to the undersurface of the resurfacing prosthetic. This embodiment may be advantageously used either as a humeral hemiarthroplasty (articulation with the native glenoid) or with articulation with a prosthetic glenoid component.

In accordance with one embodiment of the invention, a device for replacing a portion of a bone joint, comprises a prosthetic head comprising an articulation surface having a shape of a semi-ellipsoid, and a bottom surface, wherein the bottom surface includes a taper feature for engagement with an engagement member connectable to the joint, the engagement member connectable to the prosthetic head and operable to maintain a proper orientation of the semi-ellipsoid shape of the articulation surface with respect to the joint.

In accordance with alternative embodiments relating thereto, the device further includes; the engagement member; a bone connecting member, the bone connecting member connectable to a bone of the joint, and taper means for connecting the bone connecting member to the engagement member; the taper means includes at least one taper recess disposed in the engagement member; the taper means includes a taper surface extending from the bone contacting member, adapted to frictionally engage the at least one taper recess disposed in the engagement member; the bone connecting member includes at least one taper recess, and the taper means includes a double ended taper operative to frictionally engage at least one of the at least one taper recesses in the bone contacting member, and at least one of the at least one taper recess disposed in the engagement member; the taper means includes a ball taper, at least one end having an axially curved surface, whereby the prosthetic head is connectable to the engagement member at an angle, using the ball taper; the prosthetic head is a humeral head; the joint is a shoulder, and wherein the engagement member is sized and dimensioned to be engageable to bone of a humerus; the joint is a shoulder, and wherein the engagement member is sized and dimensioned to be engageable upon a cut surface of a bone of a humerus; the engagement member is sized and dimensioned to connect to the epiphysis or metaphysis of a bone adjacent to the joint; the engagement member is configured to connect to a prosthetic stem associated within the diaphysis of a bone adjacent to the joint; the engagement member includes a prosthetic stem insertable within the diaphysis of a bone adjacent to the joint; the engagement member is connectable to a prosthetic stem, the prosthetic stem connected to bone of the joint; and the device further comprises an opposing prosthetic articulating surface mateable with the articulating surface disposed on a first side of the articulating member.

In a further embodiment of the invention, a device for replacing a portion of a shoulder joint, comprises: an articulating member including an articulating surface disposed on a first side of the articulating member, the articulating surface having a superior/inferior dimension greater than an anterior/posterior dimension, a spherical chamber formed in a second side of the articulating member; an engagement member, connectable to a bone of the joint, and including a spherical protrusion disposed upon a first side of the engagement member, the spherical protrusion sized to be inserted, at any of a plurality of angles, at least partially within the spherical chamber, whereby when the spherical surfaces are mated, the engagement member is secured to the articulating member by a friction between the mating spherical surfaces; wherein when the engagement member is connected to the bone of the joint, and the spherical surfaces are mated at a therapeutically effective angle, the articulating member is therapeutically secured to the bone of the joint.

Alternative embodiments relating thereto include the mating spherical surfaces are connected together using a fastener, after being mated at a therapeutically effective angle; and the device further comprises a bone connecting member, the bone connecting member connectable to a bone of the joint, and machine taper means for connecting the bone connecting member to the engagement member; the machine taper means includes a ball taper, at least one end having an axially curved surface, whereby the bone connecting member and the engagement member are connectable at an angle, using the ball taper.

In yet another embodiment of the invention, a method of replacing a portion of a joint of a patient, comprises: making an incision in the patient and exposing an articulating surface of the joint; cutting bone of the joint to remove at least a portion of a native articulating surface, and to form a spherical shape; positioning a prosthetic replacement, at any of a plurality of angles, upon the spherical shape of the cut bone, the prosthetic replacement having a first side including a replacement articulating surface, the replacement articulating surface having a superior/inferior dimension greater than an anterior/posterior dimension, the prosthetic replacement further having a spherical chamber formed in a second side, the spherical chamber sized and dimensioned to conform to the size and dimension of the spherical shape of the cut bone; inserting the cut bone of the joint into the spherical chamber; and aligning the articulating surface of the prosthetic replacement with a mating articulating surface in the body, by changing a position of the cut bone within the spherical chamber; wherein the prosthetic replacement therapeutically replaces the removed portion of a native articulating surface.

Further embodiments relating thereto include the joint is a shoulder; wherein cut bone and the articulating surface are connected by means selected from the group consisting of: press fit, porous coated biologic fixation, cement; and wherein the radius of the replacement articulating surface, and the radius of a mating articulating surface in the patient, are not the same.

BRIEF DESCRIPTION OF THE DRAWINGS

The features and inventive aspects of the present invention will become more apparent upon reading the following detailed description, claims, and drawings, of which the following is a brief description:

FIG. 11 is an exploded cross-section side view of another embodiment of the head, the intermediate component and a portion of the stem in accordance with the present invention;

FIG. 12 is a normal view of the bottom surface of the head and the intermediate component as illustrated in FIG. 11 in an assembled state;

FIG. 19 is a cross section side view of an embodiment of the head, the intermediate component, a male taper, and a portion of the stem in accordance with the present invention;

FIGS. 19A and 19B depict ball tapers in accordance with the invention, interposable between components of the invention to permit a desired angle between the components;

FIG. 19C illustrates a cross section of an embodiment of the invention, illustrating a means of securing adjacent components of the invention;

FIG. 20 is a normal view of the bottom surface of the head and the intermediate component as illustrated in FIG. 19 in an assembled state;

FIG. 21 is a cross section side view of an embodiment of the humeral prosthetic head component and a portion of the resurfaced natural humeral head in accordance with the present invention;

FIG. 21A is a cross section of the embodiment of FIG. 21, disposed upon a humerus;

FIG. 22 a normal view of the bottom surface of the component as illustrated in FIG. 21;

FIG. 23 is a cross section of an alternative device in accordance with the invention, having two intermediate portions; and FIG. 23A is a cross section of another alternative device in accordance with the invention, having an intermediate portion supported upon bone of the joint.

DETAILED DESCRIPTION OF THE INVENTION

Figure 1:
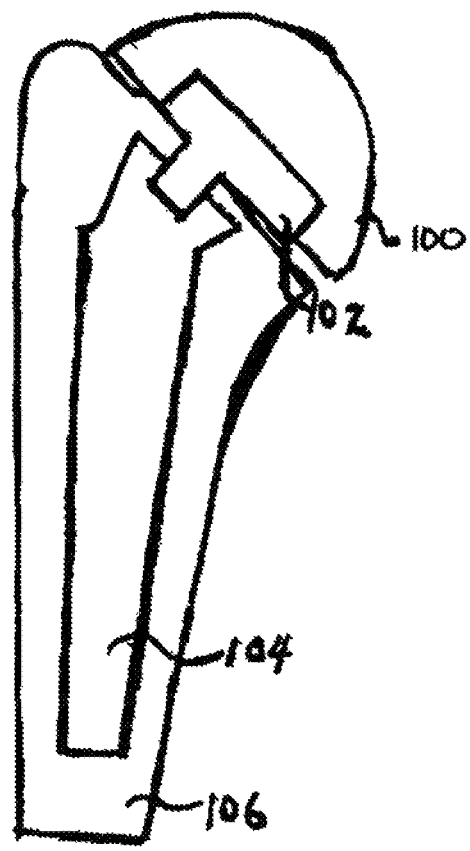
FIG. 1 is a cross section side view of a humeral prosthetic head having an articulation surface of a semi-ellipsoid, an intermediate component, and a prosthetic stem fixed within a humeral shaft shown in an assembled state in accordance with the present invention.
Figure 17:
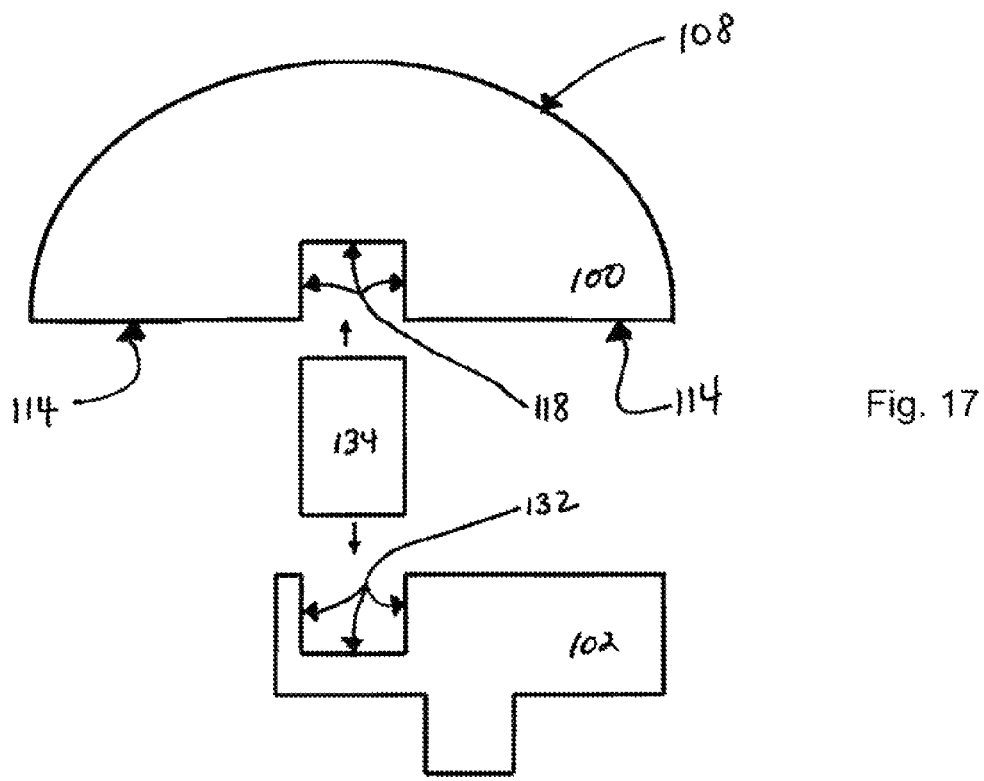
FIG. 17 is an exploded cross-section side view of yet another embodiment of the head, a double male taper and the intermediate component in accordance with the present invention.
Figure 18:
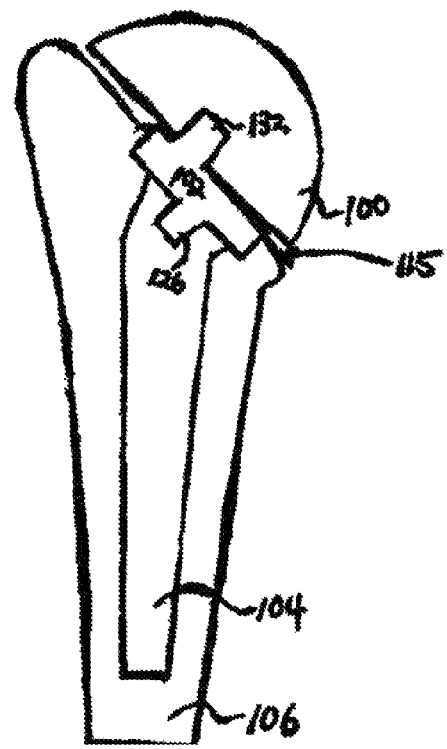
FIG. 18 is a cross section side view of the head, the intermediate component, and the stem illustrated in FIG. 15 wherein the stem is fixed within a humeral shaft and shown in an assembled state.

Referring to FIGS. 1-23A, the present invention provides a humeral prosthetic head 100 having an articulation surface 108 of a semi-ellipsoid that is designed to be in communication with an intermediate component 102. Intermediate component 102 serves as an interface between head 100 and a prosthetic stem 104. Stem 104 is fixed within the metaphyseal and/or diaphyseal part of a humeral shaft 106. This fixation of stem 104 within humeral shaft 106 is achieved by art-disclosed means such as press fit, porous coated biologic fixation, cement fixation, combinations thereof, or other mechanisms. Intermediate component 102 engages with both head 100 and stem 104 as shown in FIGS. 1 and 18.

Figure 2:
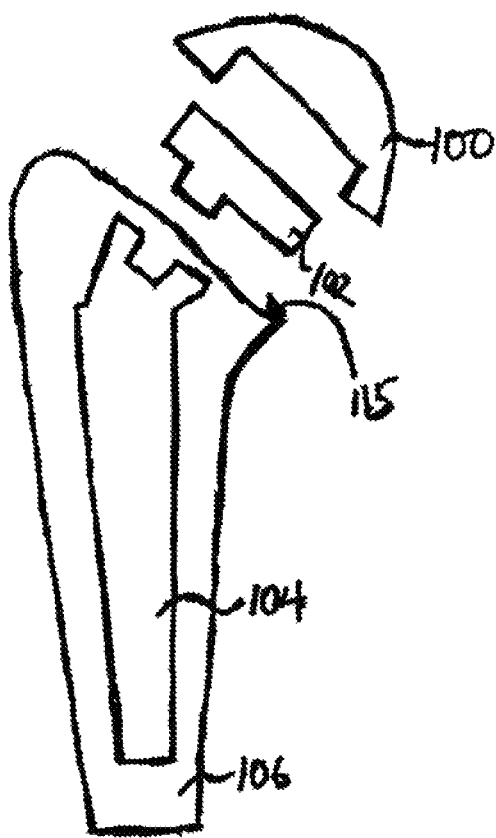
FIG. 2 is an exploded side view of the head, the intermediate component, and the prosthetic stem fixed within a humeral shaft illustrated in FIG. 1.

The stem 104 can be any art-disclosed prosthetic stem designed to be placed in humeral shaft 106. Stem 104 can be a unitary structure as shown in FIGS. 1-2 and 18. Alternatively, stem 104 can be constructed out of modular components (not shown).

Figure 3:
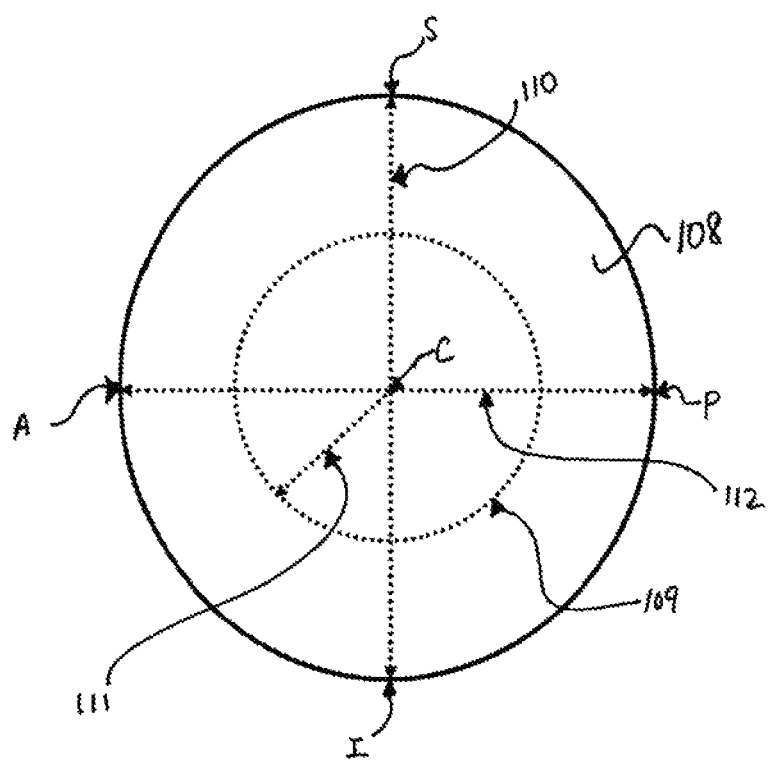
FIG. 3 is a normal view of the articulation surface of the head illustrated in FIG. 1.

Referring to FIGS. 3-6, head 100 has articulation surface 108 of a semi-ellipsoid. Semi-ellipsoid is defined in this application as having a central point (C) and a central portion 109 that is spherical with a predetermined radius of curvature 111 ("ROC") but the superior to the inferior surface curvature length 110 ("SI dimensions") of articulation surface 108 is greater than anterior to posterior surface curvature length 112 ("AP dimensions") resulting in a peripheral contour 116 of articulation surface 108 being elliptical in shape as shown in FIG. 3. Correspondingly, the superior (S) to the inferior (I) radius of curvature of articulation surface 108 is also greater than the anterior (A) to the posterior (P) radius of curvature. Central point (C) is where the x-axis (direction between anterior (A) to posterior (P), the y-axis (direction between superior (S) and interior (I)), and the z axis (direction between top (T) and bottom (B)) of the head 100 intercept.

Notwithstanding the above, it should be understood that the formation of a humeral head with a predetermined curvature of substantial mathematical precision is not a requirement of the invention. Indeed, the human body itself is not, in many respects, mathematically perfect, the shoulder or hip joints being examples. Rather, curves not corresponding to a mathematical formula, but generally conforming to an SI dimension greater than an AP dimension are deemed to fall within a definition of ellipsoidal, for the purposes of the instant invention and disclosure.

Semi-ellipsoidal, in the context of the invention, refers to the configuration of head 100, in that it forms about a half of a complete ellipse, as defined herein. However, head 100 may form substantially more or less than one half of an ellipse, while conforming to the invention.

In one embodiment, ROC 111 of central portion 109 is the same as radius of curvature of the central portion of a patent's native glenoid or a prosthetic glenoid component. This matching of radii of curvature between central portion 109 and the central portion of the native glenoid or prosthetic glenoid component will improve the wear characteristics of the native glenoid in the case of a hemiarthroplasty or replacement components in the case of a total shoulder arthroplasty. In addition, this design can allow for the use of metal on metal and/or ceramic bearing surfaces in the case of total shoulder arthroplasty. It is optional that ROC 111 is same as radius of curvature of the central portion of a patent's native humeral head.

Figure 4:
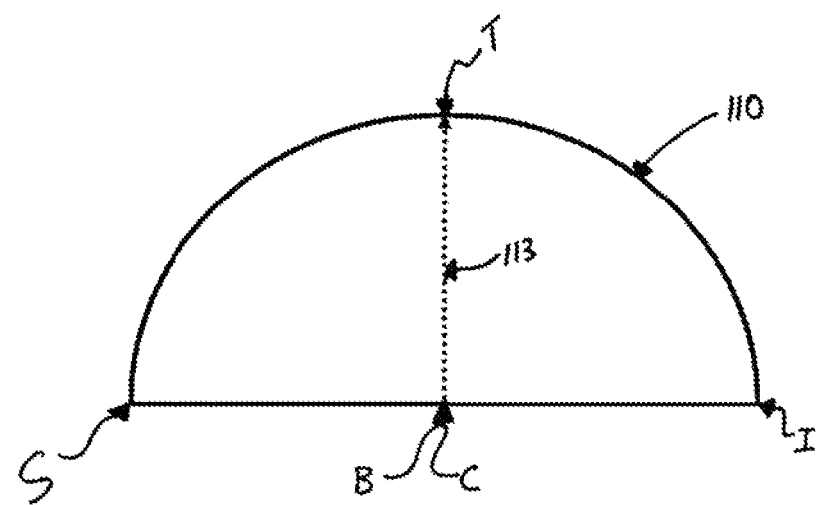
FIG. 4 is a cross-section view of the superior to inferior mid-section of the head illustrated in FIG. 1.
Figure 5:
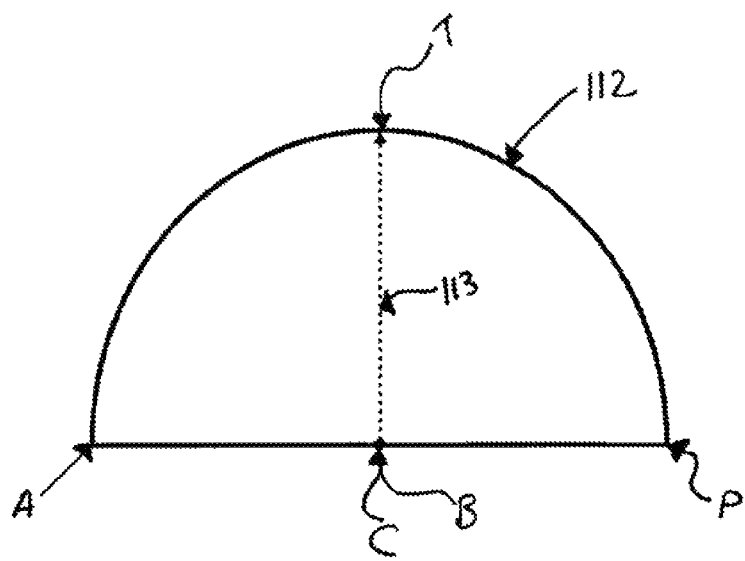
FIG. 5 is a cross-section view of the anterior to posterior mid-section of the head illustrated in FIG. 1.

The SI dimension 110, AP dimension 112, ROC 111 and head height 113 of head 100 (as shown in FIGS. 4-5) vary to accommodate difference in patient size and pathologic changes to the shoulder. Accordingly, a spectrum of anatomic shapes and sizes of head 100 should be manufactured. Exemplary ranges for SI dimension 110 are from about 31 mm to about 62 mm, from about 35 mm to about 58 mm, from about 39 mm to about 54 mm. Exemplary ranges for AP dimension 112 are from about 29 mm to about 58 mm, from about 33 mm to about 54 mm, and from about 37 mm to about 50 mm. Exemplary ranges for ROC 111 are from about 16 mm to about 36 mm, from about 18 mm to about 34 mm, from about 20 mm to about 30 mm. Exemplary ranges for head height 113 are from about 12 mm to 26 mm, from about 13 mm to about 22 mm, and from about 15 mm to about 23 mm. The term "about" as used in this application shall mean+/−5% of the stated value.

A humeral head component may be constructed, for example, using values derived as follows:

The ratio between SI dimension 110 and AP dimension 112 of articulation surface 108 can also vary and is dependent upon size and shape of a patent's native humeral head. Exemplary ranges for this ratio are from about 0.99 to about 0.83, from about 0.98 to about 0.85, and from about 0.97 to about 0.86.

An exemplary linear equation for the relationship between SI dimension 110 ("a") and AP dimension 112 ("b") is: $a=2.53+1.01(b)$. An exemplary quadratic equation for the relationship between SI dimension 110 ("a") and AP dimension 112 ("b") is: $a=2.48+1.01(b)-0.004(b-43.1)^2$.

An exemplary linear equation for the relationship between ROC 111 ("d") and SI dimension 110 ("a") is: $a=8.61+1.53(d)$. An exemplary quadratic equation for the relationship between ROC 111 ("d") and SI dimension 110 ("a") is: $a=8.39+1.55(d)-0.04(d-24.4)^2$.

An exemplary linear equation for the relationship between ROC 111 ("d") and AP dimension 112 ("b") is: $b=8.46+1.41(d)$. An exemplary quadratic equation for the relationship between ROC 111 ("d") and AP dimension 112 ("b") is: $b=8.46+1.42(d)-0.02(d-24.4)^2$.

An exemplary linear equation for the relationship between head height 113 ("c") and ROC 111 ("d") is: $c=3.98+0.56(d)$. An exemplary quadratic equation for the relationship between head height 113 ("c") and ROC 111 ("d") is: $c=4.33+0.53(d)+0.06(d-24.4)^2$.

The articulation surface 108 is constructed of materials such as metal, polymer, ceramic, or a combination thereof, including composite materials. The orientation of articulation surface 108 respects the native orientation of natural replaced humeral head's semi-ellipsoid shape. This means that SI dimension 110 aligns along the SI dimension of the cut surface of humeral shaft 106 and AP dimension 112 aligns along the AP dimension of the cut surface of humeral shaft 106. The cut surface of the humeral shaft is shown as 115 on FIGS. 2 and 6 and is also known as the plane of the humeral osteotomy. The plane of humeral osteotomy 115 is indicated in FIG. 6 as beneath articulation surface 108 upon implantation.

Figure 7:
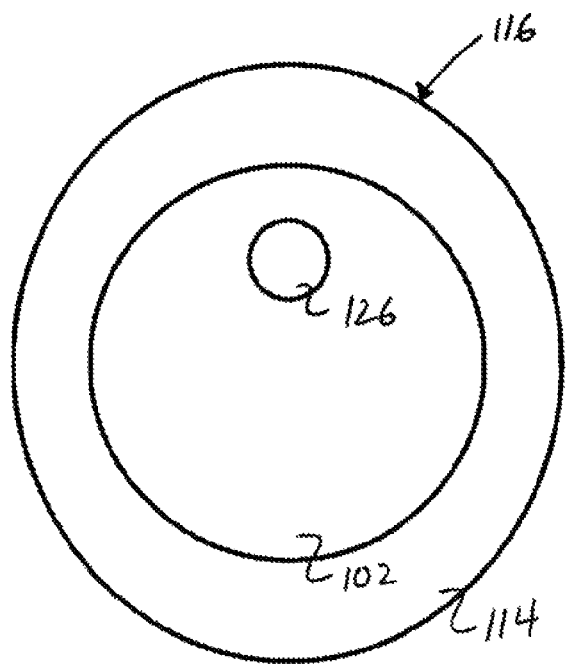
FIG. 7 is a normal view of the bottom surface of the head and the intermediate component as illustrated in FIG. 1 in an assembled state.
Figure 13:
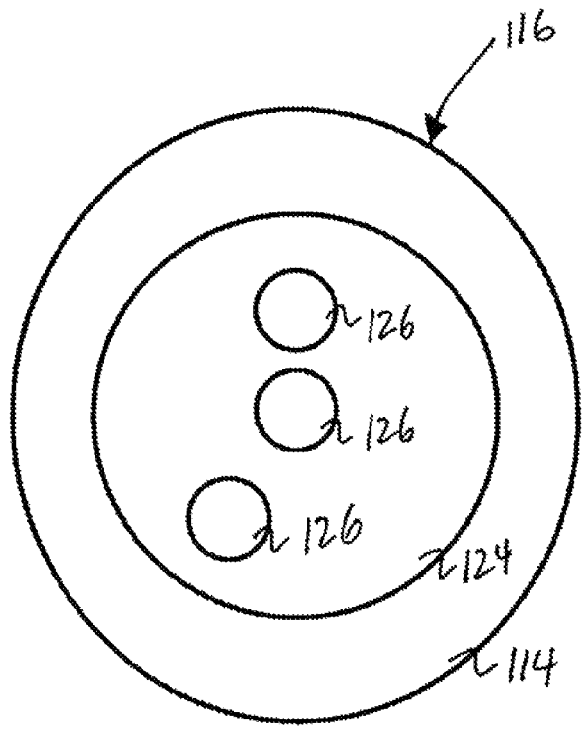
FIG. 13 is a normal view of the bottom surface of the head and another embodiment of the intermediate component in an assembled state in accordance with the present invention.

Referring to FIGS. 7, 12 and 13, bottom surface 114 of head 100 opposes articulation surface 108. Unlike conventional prosthetic humeral heads, the general outer shape of bottom surface 114 (also known as peripheral contour 116) is not spherical but elliptical.

Figure 6:
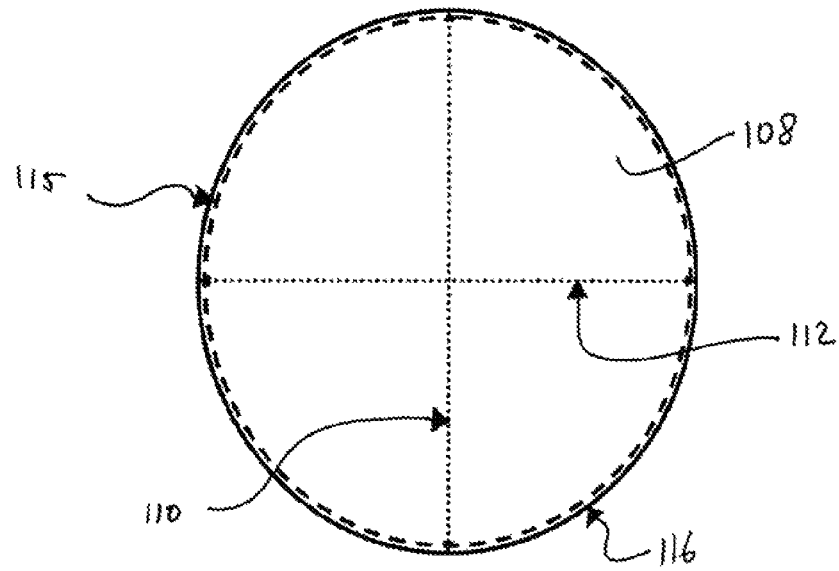
FIG. 6 is a normal view of the articulation surface of the head illustrated in FIG. 1 with the plane of the humeral osteotomy located below the articulation surface indicated.

Referring to FIG. 6, osteotomy surface 115 is shown to be slightly smaller in size than peripheral contour 116 (which is the same as the general outer shape of bottom surface 114) and illustrates that SI dimension and AP dimension of osteotomy surface 115 is aligned with the SI dimension and AP dimension of articulation surface 108 and bottom surface 114. In another embodiment, humeral osteotomy surface 115 is equal in size to peripheral contour 116.

Figure 8:
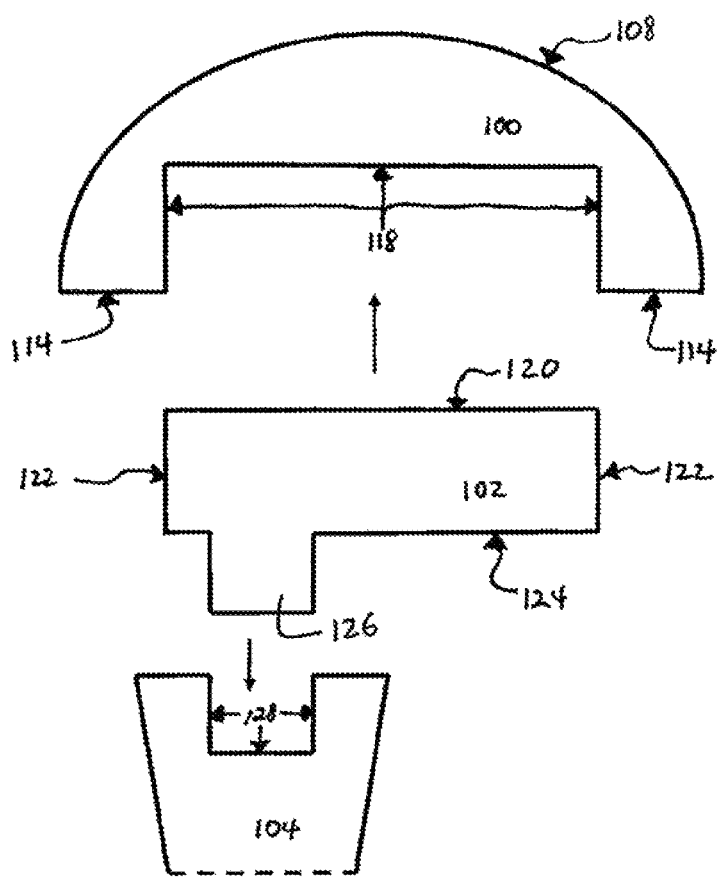
FIG. 8 is an exploded cross-sectional side view of the head, the intermediate component, and a portion of the stem as illustrated in FIG. 2.
Figure 9:
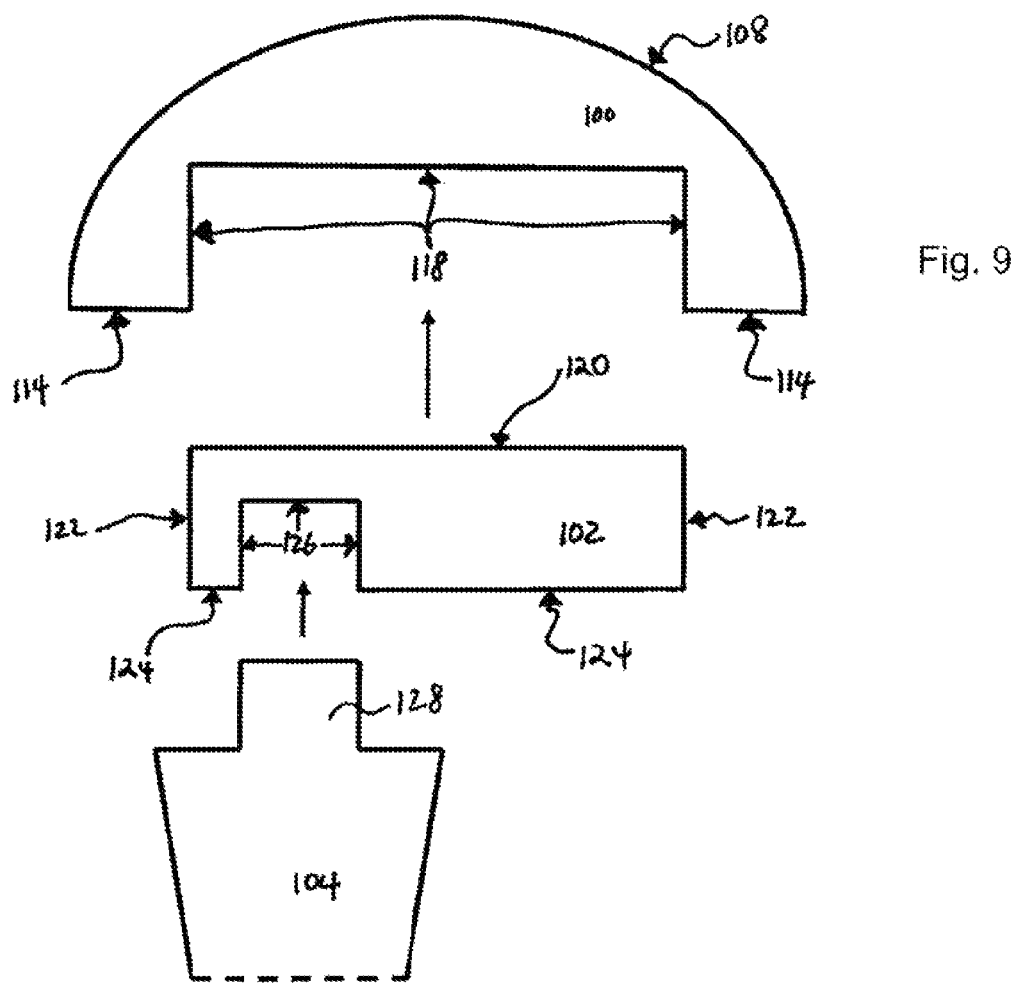
FIG. 9 is an exploded cross-section side view of an embodiment of the head, the intermediate component and a portion of the stem in accordance with the present invention.
Figure 10:
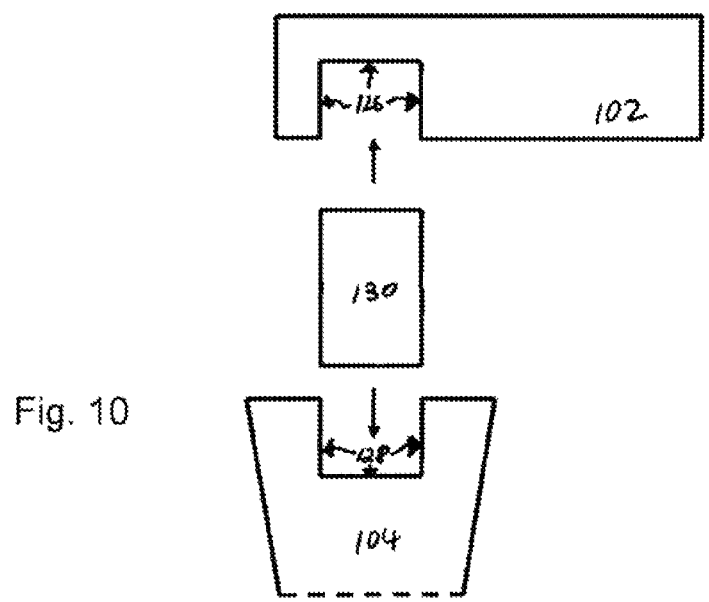
FIG. 10 is an exploded cross-section side view of an embodiment of the intermediate component, a double male taper and a portion of the stem in accordance with the present invention.

Referring to FIGS. 8-9, and 11, bottom surface 114 includes a taper feature 118 designed to engage with intermediate component 102. Taper feature 118 is a machine taper, having a shank that gradually tapers along the entire length of the mating portions. An example is a Morse taper, but other machine taper configurations are known. The machine taper is characterized in a connection by friction between the tapered mating surfaces, as opposed to an interlocking or threaded engagement. Intermediate component 102 is generally a cylindrical disc centered within head 100. Specifically, the x, y and z axis of head 100 are collinear with the x, y, and z axis of intermediate component 102, as may be seen in FIG. 7. As interpreted with respect to FIG. 3, the x axis could be construed to be the A/P axis, they axis the S/I axis, and the z axis extending from the centerline c. With respect to the symmetrically round intermediate component 102, the x and y axes bisect the component, and the z axis extends from the center. This center location of intermediate component 102 allows for rotation of intermediate component 102 within head 100.

Referring to FIGS. 8-9, intermediate component 102 includes a head surface 120, side surfaces 122 and a stem surface 124. Head surface 120 and side surfaces 122 define or form a male taper. Referring to FIGS. 1-2 and 8-9, taper feature 118 is a female taper formed from a portion of bottom surface 114 for receiving male taper (120, 122). The engagement of taper feature 118 with male taper (120, 122) engages or couples head 100 with intermediate component 102. Both head 100 and intermediate component 102 in this situation will be placed above the plane of humeral osteotomy 115 as shown in FIG. 2.

A taper is advantageous in that it allows the tapered components to be assembled and aligned without tools, and provides a sufficiently strong connection to maintain a respective position while the assembled components are trial fit within the body. Performing the trial fit would typically exert substantial misalignment forces upon the components, which a properly formed taper can withstand. If an initial trial fit is unsatisfactory, the tapered joint may be undone, either by applying an increased amount of force, or by inserting a tool through an access port, such as the aperture of locking feature 211, shown in FIG. 19. Alternatives to a taper include welding, cement, bonding with a third material, including screws or cements, or other methods known to one skilled in the art.

Prior to separating a trial fit, it may be advantageous to mark either a former position, or a desired position, to facilitate proper subsequent alignment. Once a satisfactory trial fit has been achieved, the taper may be further secured by applying cement to joined surfaces, or through the use of locking feature 211, discussed further below, through the use of a set screw impinging on a side surface of the taper, or by other means known in the art for securing a taper.

Figure 15:
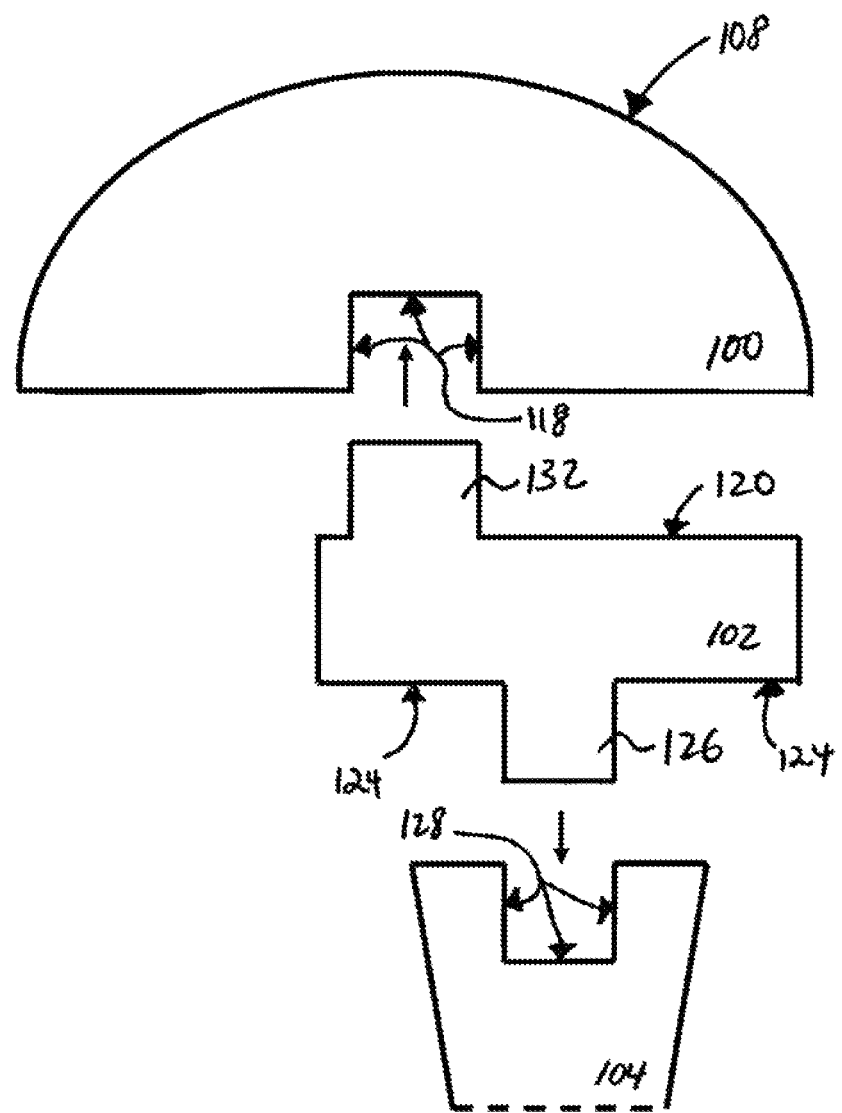
FIG. 15 is an exploded cross-section side view of an embodiment of the head, the intermediate component and a portion of the stem in accordance with the present invention.

Referring to FIGS. 8-9, 12, and 15-16, stem surface 124 includes a taper feature 126 for engagement with a taper feature 128 of stem 104. In FIGS. 8, 12 and 15, taper feature 126 is a male taper formed by having a portion of stem surface 124 extends obtusely from intermediate component 102. Taper feature 128 is a female taper formed from a portion of stem 104 for receiving taper feature 126. The engagement of these taper features (126, 128) engages or couples intermediate component 102 with stem 104. In an alternative embodiment and referring to FIGS. 9 and 16, taper feature 126 is a female taper and taper feature 128 is a male taper. In another alternative embodiment and referring to FIG. 10, taper feature 126 is a female taper, taper feature 128 is also a female taper and a double male taper 130 is provided for engagement with both of these taper features (126, 128) thereby allowing the coupling of intermediate component 102 and stem 104.

Referring to FIGS. 1-2 and 7-10, taper feature 126 is eccentrically located in intermediate component 102 such that the x, y, and z axis of taper feature 126 are not collinear with (but are radially offset from) the x, y, z axis of intermediate component 102. Rotation of intermediate component 102 about this eccentric taper feature 126 connecting intermediate component 102 with stem 104 will result in translation of head 100 within the plane of intermediate component 102 as well as the plane of humeral osteotomy 115, while allowing for SI dimension 110 and AP dimension curvature 112 of head 100 to remain positioned in the desired anatomic orientation prescribed by the patient's anatomy.

Figure 14:
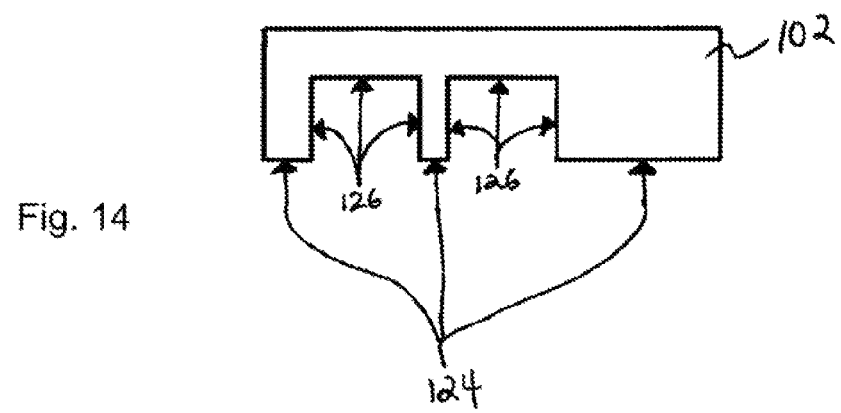
FIG. 14 is a cross section view of the superior to interior mid-section of the intermediate component as illustrated in FIG. 13.

In another embodiment of the invention, and with reference to FIGS. 11-12 and 15-17, taper feature 126 is centrally located in intermediate component 102 such that the x, y, z axis of taper feature 126 are collinear with the x, y, z axis of intermediate component 102. In yet another embodiment and referring to FIGS. 13-14, stem surface 124 of intermediate component 102 has multiple (i.e., 2 or more) taper features 126 that are either centrally located, eccentrically located, or a combination thereof. These multiple taper features 126 are likely to be female tapers. The eccentrically located taper feature 126 as shown in FIG. 13 is not shown in FIG. 14 because FIG. 14 is a cross section view of the superior to interior mid-section of intermediate component 102 and this eccentrically located taper feature 126 is not located in this superior to interior mid-section.

In the embodiments discussed above and shown in FIGS. 1-2, 8-9, and 11, head 100 and the portion of intermediate component 102 that are received into head 100 are placed above the plane of humeral osteotomy 115, during implantation as shown in FIG. 1.

Figure 16:
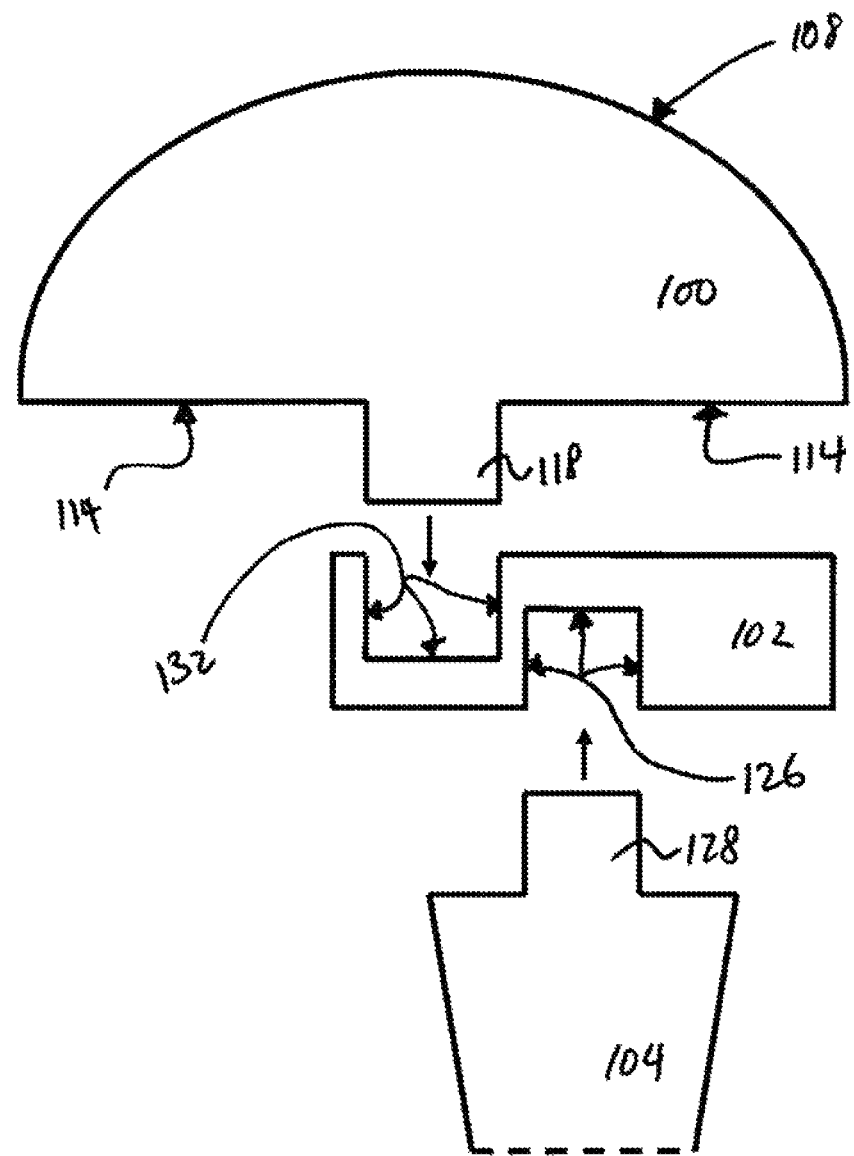
FIG. 16 is an exploded cross-section side view of another embodiment of the head, the intermediate component and a portion of the stem in accordance with the present invention.

In yet another embodiment and referring to FIG. 15, head face 120 includes a taper feature 132. Taper feature 132 is formed by having a portion of head surface 120 extend obtusely from intermediate component 102. In this embodiment, taper feature 118 is a female taper formed from a portion of bottom surface 114 for receiving taper feature 132. Alternatively, taper feature 132 can be a female taper for receiving taper feature 118 which is now a male taper as shown in FIG. 16. In another embodiment taper features 118 and 132 are both female tapers that can receive a double male taper 134 as shown in FIG. 17. Taper feature 132, regardless whether it is a male taper or a female taper, and depending upon a user's choice, can be placed either centrally or eccentrically in relation to intermediate component 102. It is also within the scope of the present invention to have multiple taper features 132, e.g. multiple female tapers or the like. The embodiments discussed in this paragraph, and for example shown in FIGS. 15-17, provide engagement between head 100 and intermediate component 102, wherein intermediate component 102 is located below the plane of the humeral osteotomy 115. An example of a location of intermediate component 102 below the plane of the humeral osteotomy 115, in a bone, is shown in FIG. 18.

In another embodiment of the invention, and with reference to FIGS. 19-20, head 200 has an articulation surface 202 and a bottom surface 204, similar to articulation surface 108, and bottom surface 114, discussed above. Intermediate component 206 has a head surface 208 having a convex semi-spherical shape that can be received by a female taper feature 210 formed from bottom surface 204. The female taper feature 210 can have any art-disclosed shape that can receive head surface 208. For example, female taper feature 210 can be a concave semi-spherical surface, a concave cone shape, a conventional female taper shape, or the like. In the embodiment illustrated, female taper feature 210 forms a chamber including opposed planar surfaces, wherein opposite sides are advantageously disposed at an angle relative to each other, to form a taper. With impaction, intermediate component 206 and head 200 locks in place. In particular, head 206 forms a curvilinear surface, in the embodiment shown, a spherical surface, which engages the opposed planar surfaces of female taper feature 210. The curved surfaces of head 206 readily admit head 206 within female taper feature 210, at any of a plurality of angles, to an appropriate predetermined depth, after which the curvilinear and opposed planar surfaces are press fit together. In one embodiment of the invention, an appropriate depth is assured by engagement of head 206 with an upper roof surface of female taper feature 210. Additional frictional securement of head 206 and female taper feature 210 is accomplished by an angular displacement of the opposed planar surfaces of female taper feature 210, visible in FIG. 19. A locking feature 211 (e.g. a screw and an opening within intermediate component 206 for placement of such a screw) is optionally provided and shown in FIG. 19 in order to further assist engagement of head 200 and intermediate component 206. A fastener, such as a screw, not shown, is advantageously passed through taper feature 214 to be inserted into head 200, to avoid disruption to articulating surface 202.

Another view of a fastening mechanism is illustrated in FIG. 19C, in which shaft 226 passes through intermediate component 206, in which countersunk portion 232 is disposed within head surface 208. A threaded bore 226, axially aligned with shaft 226, is disposed in intermediate portion 102A, and is adapted to receive a threaded fastener, not shown, which is passed through shaft 226. It should be understood, however, that other approaches for further fastening intermediate portions are possible, as may be understood by one skilled in the art.

With further reference to FIGS. 19-20, intermediate component 206 is centrally located in head 200 such that the x, y, z axis of intermediate component 206 are collinear with the x, y, z axis of head 200. Stem surface 212 of intermediate component 206 opposes head surface 208. Stem surface 212 includes one or more taper feature(s) 214 for engagement with a corresponding taper feature 216 located within stem 218. Taper feature(s) 214 is same as taper feature(s) 126, and taper feature 216 is the same as taper feature 128, both as discussed above. Accordingly, the various embodiments discussed above for taper features 126 and 128 also apply to taper features 214 and 216. For example, taper feature(s) 214 can be (i) either centrally located within intermediate component 206, eccentrically located within intermediate component 206, or a combination thereof; and (ii) a female taper, a male taper or multiple female tapers. For example, with reference to FIG. 19, taper features 214 and 216 are female tapers for receiving a double male taper 220. Referring to FIGS. 19-20, one of taper features 214 is centrally located while the one of taper features 214 is eccentrically located within intermediate component 206.

It is within the scope of the present invention to use different types of art-disclosed tapers for the taper features (118, 126, 128, 130, 132, 134, 210, 214, 216, 220) such as Morse tapers, ball tapers, or the like. For example, the taper features shown as male tapers in FIGS. 8-11, 15-17 and 19, can be replaced with ball tapers, and double male tapers can be double or single ball tapers. The ball taper(s) placed within the intermediate component 102 and/or the head 100 may provide variable angulations between intermediate component 102 and head 100.

Ball tapers in accordance with the invention are illustrated in FIGS. 19A-19B, for example, in which ball taper 220A or 220B replaces double male taper 220 in FIG. 19. If ball taper 220A is used, a pivot axis is closer to head 200 than if ball taper 200B is used, however with the use of the latter, a wider dispositional offset of head 200 is attainable. Of course, a ball taper may be used with any taper connection disclosed herein, including instances where there is only a single tapered surface, such as for example, taper 132, or taper 126, both shown in FIG. 18, wherein the mating surface is curvilinear, or spherical, as shown in FIGS. 19A-B. In another alternative, a double ended taper is used, however both tapered portions contain a curvilinear or spherical shape, enabling yet greater positional possibilities. A ball taper in accordance with the invention may be further secured as described elsewhere, herein, should that be therapeutically advantageous.

Referring now to FIGS. 21-22, the present invention also provides a humeral prosthetic head component 300 for resurfacing arthroplasty. Component 300 has an articulation surface 302 of a semi-ellipsoid and a bottom surface 303 having a concave spherical feature 304 for receiving the resurfaced (e.g., machined, reamed or the like) convex humeral surface 306 of the remaining natural humeral head 308. In one embodiment, the radius of curvature of concave spherical surface 304 matches the radius of curvature of the convex humeral surface 306. Articulation surface 302 has the same properties as discussed above for articulation surface 108. In one embodiment, concave spherical feature 304 is centrally located in component 300 such that the x, y, z axis of concave spherical feature 304 are collinear with the x, y, z axis of component 300. In another embodiment, the x, y, z axis of concave spherical feature 304 is collinear with the x, y, z axis of native humeral head 308. In yet another embodiment, the x, y, z axis of concave spherical feature 304 is collinear with both the x, y, z axis of component 300 and the x, y, z axis of native humeral head 308. Component 300 is fixed onto head 308 via art-disclosed engagement means such as pressure fit of concave spherical feature 304 with humeral surface 306, porous coated biologic fixation, cement fixation, or a combination thereof.

With further reference to FIGS. 21-22, a stem 310 is optionally provided to further assist with fixation of component 300 to humeral surface 306. Stem 310 can be formed as part of the unitary structure of component 300 or as a modular component that can be attached, via means known to one skilled in the art, to concave spherical feature 304, as shown in FIG. 21.

Referring again to FIG. 19C, head component 300A includes an articulation surface 302A and concave spherical feature 304A, having functions similar to analogous elements of FIGS. 21-21A, however in the embodiment of FIG. 19C, mating spherical surfaces are shown, including intermediate component 206A which forms a spherical protrusion, which may be disposed within head component 300A at any of a plurality of angles, as best meets the needs of the patient. In this embodiment, however, stem 310 is not provided, head component 300A being retained by pressure from ligaments, a friction or press fit with intermediate component 206A, adhesive, or other means such as would be understood by one skilled in the art.

FIG. 23 illustrates an alternative embodiment of the invention, in which at least two intermediate components, in this embodiment intermediate components 102 and 230, are interposed between prosthetic stem 104 and head 200. Mating taper surfaces 126A and 128A connect prosthetic stem 104 and second intermediate component 230. An advantage of this embodiment is that prosthetic stem 104 may be retained within bone 106 during revision surgery, and either or both of components 102, 230 replaced. More particularly, a new attachment may be made in the epiphysis, metaphysis, or both, without disturbing the attachment within the diaphysis, which can be difficult to remove. Additionally, either component 102 or component 230 may be rotated to produce a desired offset for head 200, each component providing a different angular and or offset disposition, or the effects of each combined, enabling additional therapeutic positioning possibilities.

The embodiment of FIG. 23 illustrates a further aspect of the invention; more particularly, the potential to secure an ellipsoidal head of the invention in the epiphysis, metaphysis, or diaphysis. Given a patient physiology of adequate strength and health, intermediate component 230, and prosthetic stem 104 may be eliminated, and intermediate component 102 alone serve as a sole support for head 200. In this embodiment, intermediate component 102 is supported by adjacent bone, advantageously cortical bone in the epiphysis and or metaphysis of the humerus. Similarly, intermediate component 230 may be secured within the epiphysis and or metaphysis, again, without the use of prosthetic stem 104. In the latter configuration, intermediate component 102 may also be secured to bone, or may only be secured by a taper or other connection to intermediate component 230.

While FIG. 23 illustrates intermediate components 102 and 230 disposed entirely within the humerus, either or both components may be supported on a cut edge of the humerus, as shown in FIG. 23A. As shown, intermediate component 102 is sized to rest upon a cut edge of cortical bone, and may be fastened thereto using any known means, including or limited to, optionally, a tapered connection to a second intermediate component 230, the latter supported by prosthetic stem 104, and or an independent connection to bone. Alternatively, where patient physiology permits, a second intermediate component 230, as well as prosthetic stem 104, may be omitted. Intermediate component 102 may additionally be provided with a portion extending into the metaphysis, shaped and sized to connect to bone using known means.

The embodiments of the present invention including the head (100, 200) and the intermediate component (102, 206) discussed above can be used either as a humeral hemiarthroplasty (articulation with the native glenoid) or with articulation with a prosthetic glenoid component (total shoulder arthroplasty). Accordingly, the present invention includes methods of using the head (100, 200) and the intermediate component (102, 206) in humeral hemiarthroplasty and total shoulder arthroplasty.

The methods of the present invention may be combined with certain art-disclosed methods for humeral hemiarthroplasty and/or total shoulder arthroplasty; however, at least head 100, 200 and intermediate component 102, 206 would replace a conventional spherical prosthetic head and related interface. In total shoulder arthroplasty, the prosthetic glenoid component may contain a radius of curvature that is equal to or greater than ROC 111.

Similarly, the present invention includes methods of using component 300 in resurfacing arthroplasty. The methods of the present invention may be combined with certain art-disclosed methods for resurfacing arthroplasty; however, at least component 300 would replace the conventional spherical humeral prosthetic head component used in prior art resurfacing arthroplasty.

While the invention has been shown and described in the context of the shoulder, it should be understood that some or all aspects of the invention may be used in applications involving any joint in the body, including the fingers, hand, wrist, elbow, spine, hip, knee, ankle, foot, and toes.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled.

Unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A device for replacing a portion of a bone joint, comprising:
    a prosthetic head comprising an articulation surface having a shape of a semi-ellipsoid, and a bottom surface, wherein the bottom surface includes a taper feature for engagement with an engagement member connectable to the joint, the engagement member connectable to said prosthetic head and operable to maintain a proper orientation of said semi-ellipsoid shape of said articulation surface with respect to the joint.

2. The device of claim 1, further including the engagement member.

3. The device of claim 2, wherein the joint is a shoulder, and wherein said engagement member is sized and dimensioned to be engageable to bone of a humerus.

4. The device of claim 2, wherein the joint is a shoulder, and wherein said engagement member is sized and dimensioned to be engageable upon a cut surface of a bone of a humerus.

5. The device of claim 2, wherein said engagement member is sized and dimensioned to connect to the epiphysis or metaphysis of a bone adjacent to the joint.

6. The device of claim 2, wherein said engagement member is configured to connect to a prosthetic stem associated within the diaphysis of a bone adjacent to the joint.

7. The device of claim 2, wherein said engagement member is connectable to a prosthetic stem, the prosthetic stem connected to bone of the joint.

8. The device of claim 1, further comprising a bone connecting member, said bone connecting member connectable to a bone of the joint, and
    taper means for connecting said bone connecting member to the engagement member.

9. The device of claim 1, wherein said prosthetic head is a humeral head.

* * * * *